United States Patent
Gibertoni

(10) Patent No.: US 6,371,947 B1
(45) Date of Patent: Apr. 16, 2002

(54) DISPOSABLE THORACIC DRAINAGE DEVICE CONNECTABLE TO AN ASPIRATION UNIT

(76) Inventor: Lucio Gibertoni, Via Curtatone, 41, 41037 Mirandola (IT)

(*) Notice: Subject to any disclaimer, the term of this patent is extended or adjusted under 35 U.S.C. 154(b) by 0 days.

(21) Appl. No.: 09/408,910

(22) Filed: Sep. 30, 1999

(30) Foreign Application Priority Data

Oct. 14, 1998 (IT) .......................................... MI98A2213

(51) Int. Cl.[7] .................................................. A61M 1/00
(52) U.S. Cl. ...................... 604/320; 604/318; 604/319; 604/321; 604/322; 604/323; 604/324; 604/326; 604/541
(58) Field of Search ................................ 604/318–324, 604/326, 541

(56) References Cited

U.S. PATENT DOCUMENTS 5,397,299 A * 3/1995 Karwoski et al. ............... 604/4

* cited by examiner

Primary Examiner—John G. Weiss
Assistant Examiner—Michael Bogart
(74) Attorney, Agent, or Firm—Guido Modiano; Albert Josif; Daniel O'Byrne

(57) ABSTRACT

A disposable thoracic drainage device connectable to an aspiration unit, comprising a container body internally forming at least one chamber for collecting the drainage liquid which is connected to an inlet for connection to a patient and to a water-head suction adjustment valve. The water-head suction adjustment valve has a first water head section and a second water head section which are side by side and mutually series-connected by a connecting duct.

11 Claims, 3 Drawing Sheets

DISPOSABLE THORACIC DRAINAGE DEVICE CONNECTABLE TO AN ASPIRATION UNIT

BACKGROUND OF THE INVENTION

The present invention relates to a disposable thoracic drainage device connectable to an aspiration unit.

It is known that drainage devices are already commercially available obtained by means of a body internally defining a plurality of regions or chambers which in practice delimit the region for collecting the drained liquid and a water seal valve which is meant to adjust the value of the suction generated for aspiration.

In order to allow the presence of the water seal valve with a chosen value of the water head, the containers must be rather tall and therefore they are usually formed by bodies, substantially shaped like a flattened parallelepiped, which usually cause difficulties in correctly supporting the device, consequently requiring specifically provided supporting elements.

Conventional containers are usually not suitable to just rest, in use, on the ground or on another flat surface, since their dimensions are such as to render them so unstable that even a slight impact may be sufficient to cause upsetting thereof.

SUMMARY OF THE INVENTION

The aim of the invention is to eliminate the above-mentioned drawbacks, by providing a disposable thoracic drainage device which can be connected to an aspiration unit and can have reduced dimensions although the adjustment water seal valve is provided inside it.

Within the scope of this aim, a particular object of the invention is to provide a drainage device which is extremely compact and can be rested on the ground without serious risk of tipping even in case of accidental impact.

Another object of the present invention is to provide a disposable device which is extremely practical and versatile and can accordingly easily adapt to the most disparate operating requirements.

Another object of the present invention is to provide a disposable drainage device which can be easily obtained starting from commonly commercially available elements and materials and is also competitive from a merely economical point of view.

This aim, these objects and others which will become apparent hereinafter are achieved by a disposable thoracic drainage device connectable to an aspiration unit, comprising a container body forming internally at least one chamber for collecting the drainage liquid which is connected to an inlet for connection to a patient and to a water-head suction adjustment valve, characterized in that said water-head suction adjustment valve has a first water head section and a second water head section which are side by side and series-connected to each other by a connecting duct.

BRIEF DESCRIPTION OF THE DRAWINGS

Further characteristics and advantages will become apparent from the following detailed description of a preferred but not exclusive embodiment of a disposable thoracic drainage device connectable to an aspiration unit, illustrated only by way of non-limiting example in the accompanying drawings, wherein.

DESCRIPTION OF THE PREFERRED EMBODIMENTS

Figure 1:
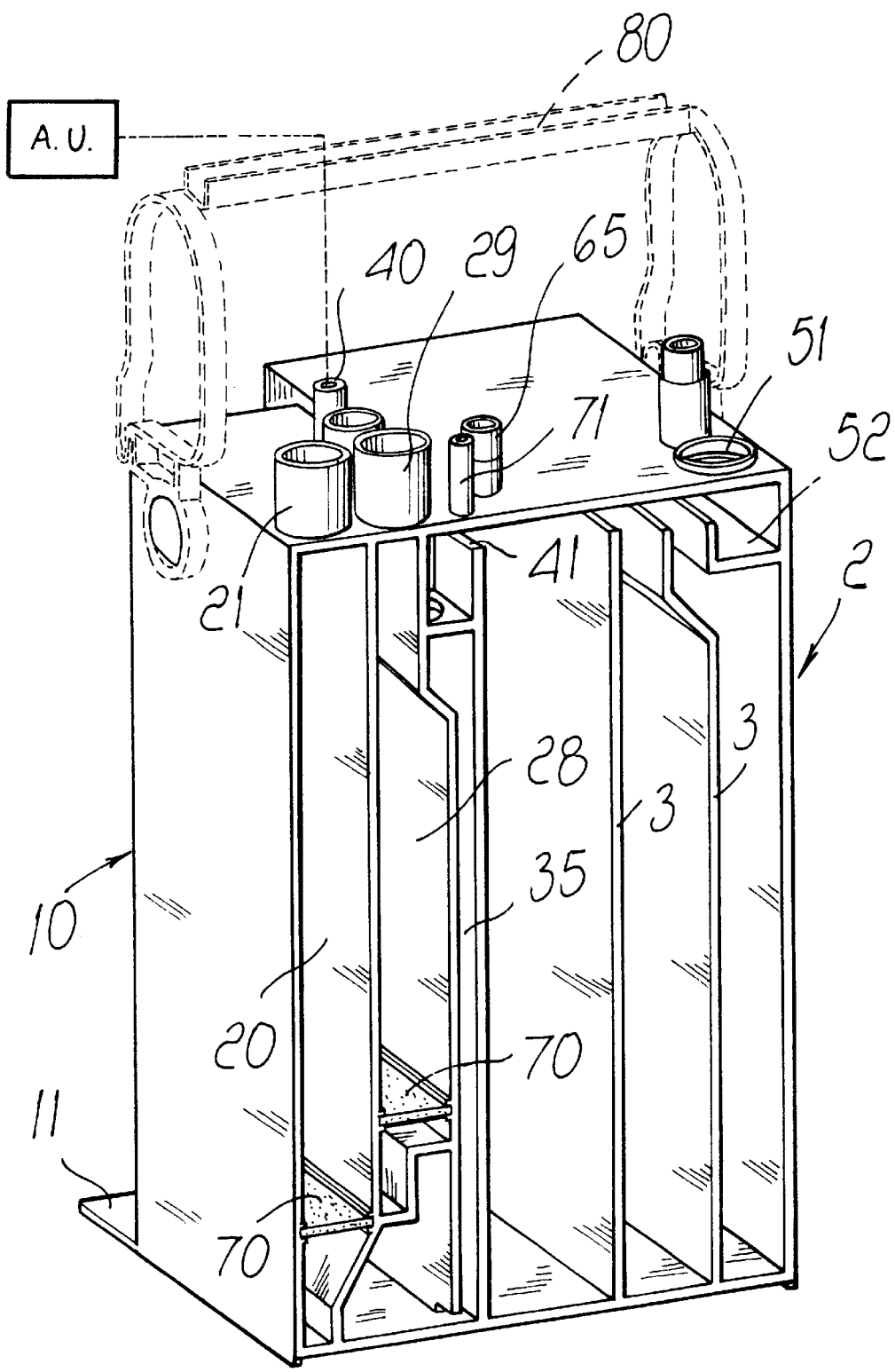
FIG. 1 is a schematic perspective view of the device according to the invention with the front wall removed.
Figure 3:
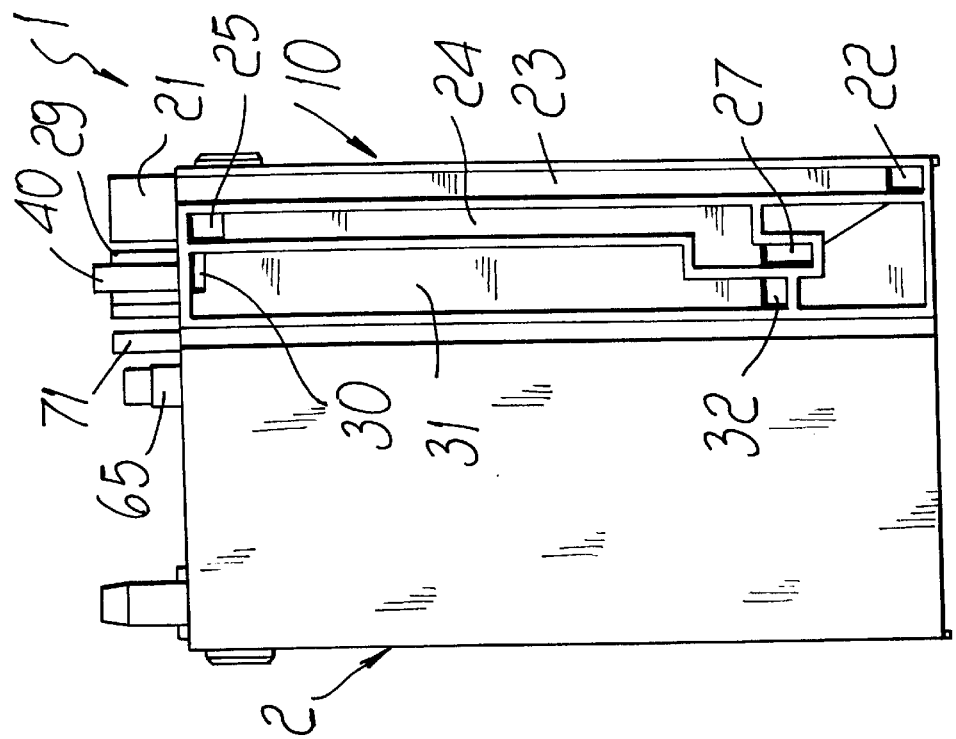
FIG. 3 is a rear elevation view of the device.
Figure 2:
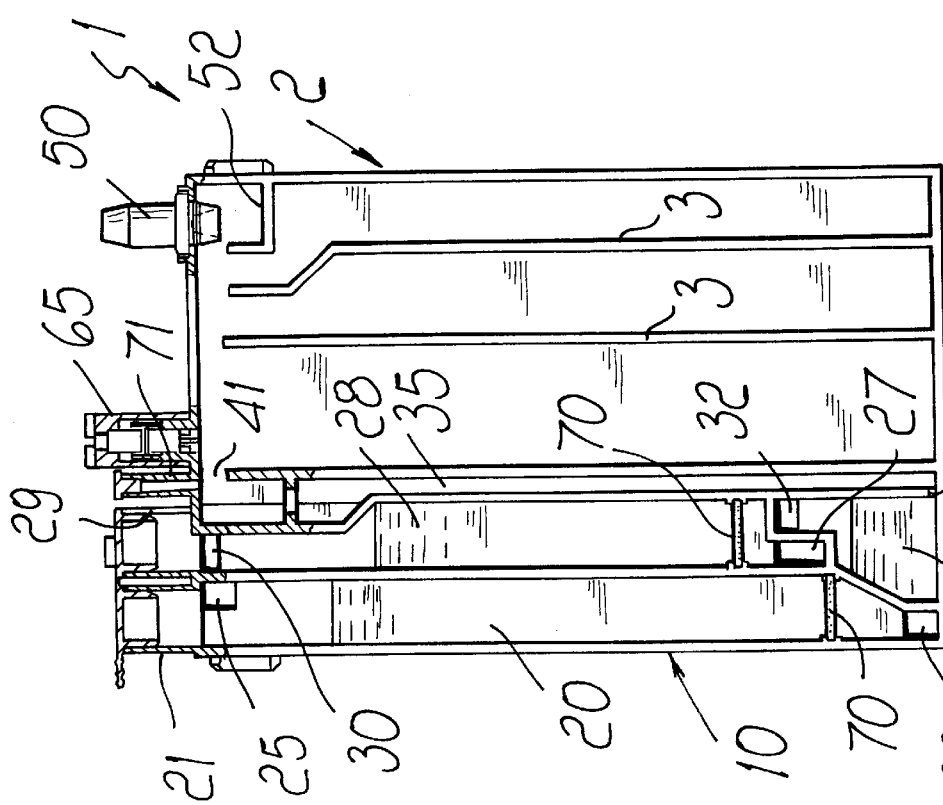
FIG. 2 is a front elevation view of the device.
Figure 5:
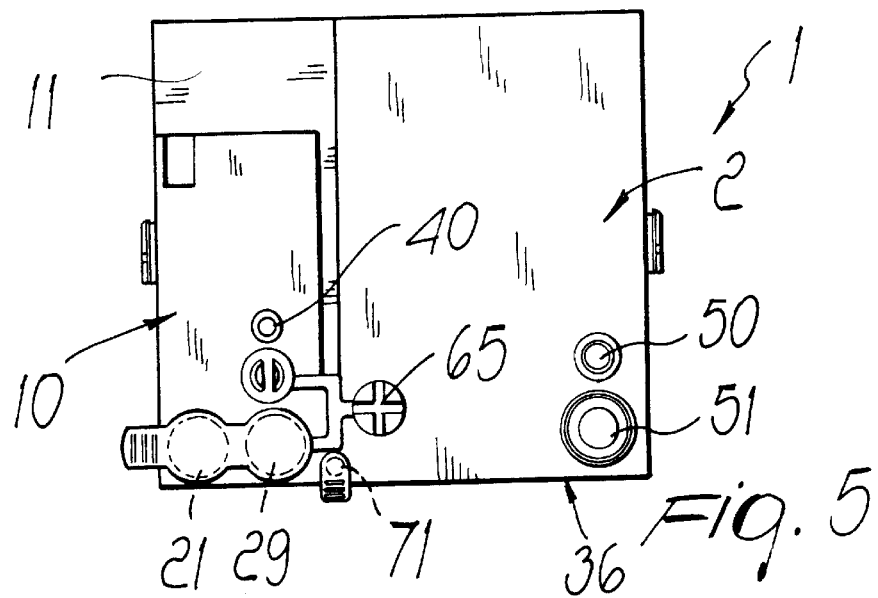
FIG. 5 is a top plan view of the device.
Figure 4:
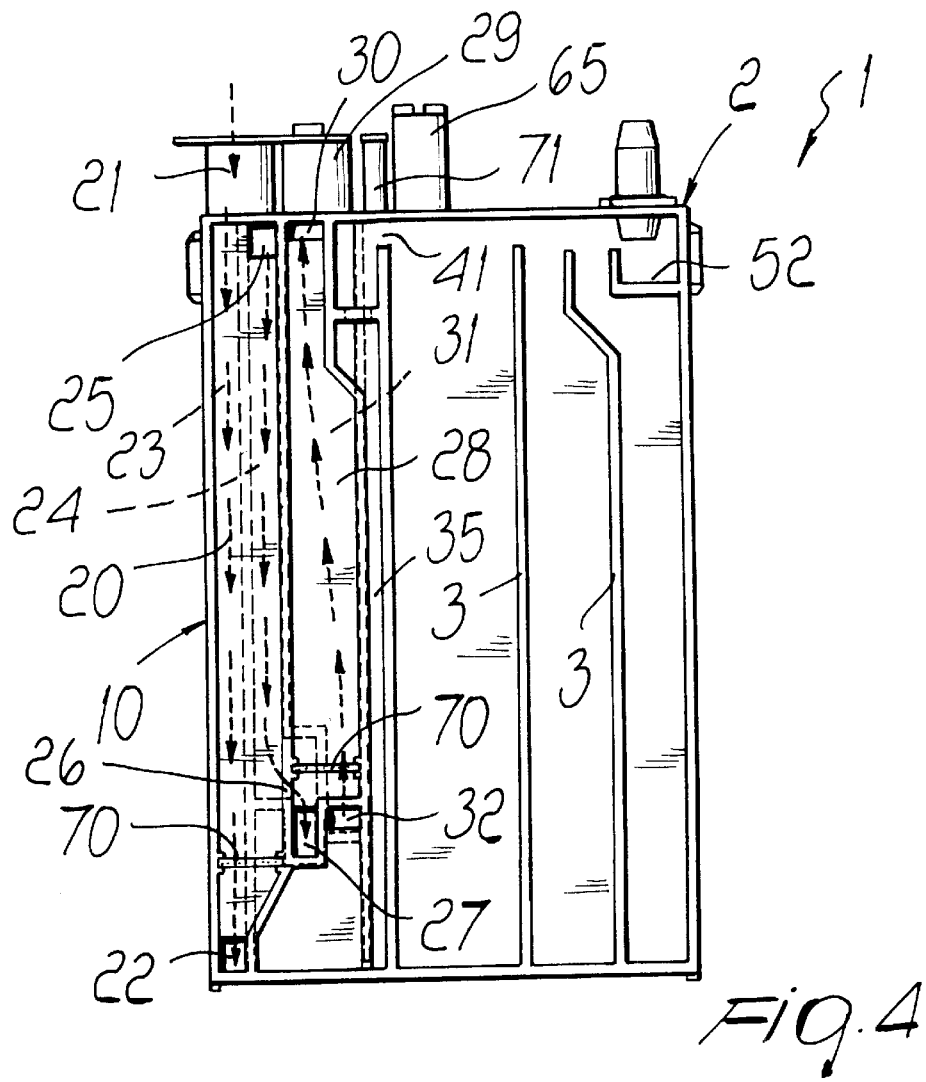
FIG. 4 is an elevation view of the device, showing in dashed lines the paths of the air through the water head sections.

With reference to the above figures, the disposable thoracic drainage device connectable to an aspiration unit, according to the invention, comprises a container body which is generally designated by the reference numeral 1 and has a central body 2 which is shaped substantially like a parallelepiped and inside which there are partitions, generally designated by the reference numeral 3, which form a plurality of compartments for a chamber for collecting the drainage liquid. A valve body, generally designated by the reference numeral 10, is laterally adjacent to the central body 2, is also substantially shaped like a parallelepiped and forms in practice the region where the water-head suction adjustment valve is provided.

The valve body and the central body rest on a footing 11 which is rather wide so as to give stability to the assembly.

The main characteristic of the invention consists in that said water-head suction adjustment valve is substantially constituted by a first water head section and by a second water head section which are mutually side by side and are series-connected to each other by a connecting duct.

In greater detail, the valve body 10 forms a first front portion 20 which is shaped by the valve body and is closed at the front by a plate-like element 36 which is preferably optically transparent and on which adjustment 1s notches are provided.

The portion 20 is connected, in an upward region, to a first water inlet 21 and is provided, in a downward region, with a first lower port 22 which connects it to a first connecting portion 23 which ends outside in an upward region and allows air to enter, as will become apparent hereinafter.

The first front portion for forming the first water head section has, in an upward region, a first upper port 25 which, by means of a second rear connecting portion 24 that constitutes said connecting duct, is connected to a second lower port 27 which ends at the lower part of a second front portion 28 in order to form the second water head section which is connected, in an upward region, to a second water inlet 29.

A second upper port 30 is also provided which, by means of a third connecting portion 31 located in a rear region in the valve body, is connected to a third lower port 32 which leads in an upward region into a separator 33 which is connected to a lower passage 34 which is connected by means of a riser duct 35 to an upper aspiration connector 40, which can be connected to the aspiration unit (A.U.), and to an opening 41 which connects it to the chambers formed by the central body.

The central body is provided with an inlet 50 for connection to the patient and with an opening 51 with a pierceable plug for drawing the liquid drained for analysis, which collects in an upper channel 52 formed inside the central body.

The above-described arrangement provides a first water head section 20 and a second water head section 28 which are arranged side by side and are in practice series-connected to each other by means of the connecting duct 24 formed in the rear part, which accordingly allows a water head of sufficient height and therefore with an optimum degree of suction without however having the typical dimensions of the conventional water-head valve, which is continuous, entailing obvious increases in height.

In the above-described solution, the provision of the water-head valve in a separate region constituted by the two portions, both of which have, in a downward region, a filtering element designated by the reference numeral 70, allows considerably more compact dimensions and to form a region in which it is possible to provide the water head of the chosen height simply by introducing the corresponding amount of liquid, not necessarily a sterile liquid, being aided in doing so by the reference notches provided on the front closure plate of the container body.

Sterile water is instead introduced in the separator 33 through the inlet 71 and acts as separator for the suction applied, through the riser duct 35, in the drainage chamber and can optionally be controlled by a negative pressure release valve, designated by the reference numeral 65.

From the above description it is therefore evident that the invention achieves the intended aim and objects and in particular it is stressed that a disposable thoracic drainage device is provided which has an extremely compact configuration and can be used by resting it on the ground with considerable stability or can optionally also be hung by applying a bridge- like element generally designated by the reference numeral 80 in FIG. 1.

The invention thus conceived is susceptible of numerous modifications and variations, all of which are within the scope of the inventive concept.

All the details may also be replaced with other technically equivalent elements.

In practice, the materials employed, as well as the contingent shapes and dimensions, may be any according to requirements.

The disclosures in Italian Patent Application No. M198 A 002213 from which this application claims priority are incorporated herein by reference.

What is claimed is:

1. A disposable thoracic drainage device connectable to an aspiration unit, comprising:
    a container body which internally forms at least one collection chamber for collecting drainage liquid;
    a connection inlet provided at said collection chamber for connection thereof to a patient;
    a first water head section;
    a first upper port and a first lower port provided at an upper and, respectively, at a lower region of said first water head section;
    a second water head section;
    a second lower port and a second upper port provided at a lower and, respectively, at an upper region of said second water head section;
    a connecting duct for connecting, in fluid communication, said first upper and second lower ports, said first lower port allowing external air entry to said first water head section; and
    an aspiration connector;
    said first and second water head sections being arranged side by side and being series-connected to each other through said connecting duct to form a water-head suction adjustment valve which is connected through said second upper port to said aspiration connector and said collection chamber.

2. The disposable thoracic drainage device of claim 1, wherein said container body is substantially shaped like a parallelepiped and has a central body which internally forms said chamber for collecting the drainage liquid, the device further comprising a valve body shaped substantially like a parallelepiped arranged laterally adjacent to said central body and accommodating said water-head suction adjustment valve.

3. The disposable thoracic drainage device of claim 2, comprising a footing, said valve body and said central body resting with base parts thereof on said footing which protrudes with respect to said base parts of said bodies.

4. The disposable thoracic drainage device of claim 2, wherein said connecting duct that connects said first and second water head sections is provided inside said valve body.

5. The disposable thoracic drainage device of claim 4, wherein said valve body comprises: a first front portion constituting said first water head section; a first water inlet provided at an upper region of said first front portion; a first external connecting portion connected to said first lower port for the entry of external air; a second front portion constituting said second water head section; a second water inlet provided at an upper region of said second front portion; a second rear connecting portion constituting said connecting duct; a third connecting portion connected to said second upper port and being provided with a third lower port; and a separator in which said third lower port leads.

6. The disposable thoracic drainage device of claim 5, comprising a plate-like element for closing said front portions, said plate-like element being at least partially optically transparent and having reference notches.

7. The disposable thoracic drainage device of claim 5, further comprising: a lower passage; a riser duct; said separator being connected by way of said lower passage to said riser duct; and a connection opening being in communication with said drainage liquid collection chamber; and wherein said aspiration connector is provided at an upper region of said raiser duct for connection to an aspiration unit and is further connected to said connection opening.

8. The disposable thoracic drainage device of claim 2, comprising, in said central body, a negative pressure elimination valve.

9. The disposable thoracic drainage of claim 6, comprising a filtering element in each one of said water head sections.

10. In a disposable thoracic drainage device connectable to an aspiration unit, comprising a container body which internally forms at least one collection chamber for collecting drainage liquid, a connection inlet and an aspiration connector provided at said collection chamber for connection of the chamber to a patient, and, respectively, for connection of the chamber to an aspiration unit,
    a water-head suction adjustment valve comprising:
        a first water head section extending between an upper and a lower region thereof;
        a second water head section extending between an upper and a lower region thereof, said first and second water head sections being arranged side by side in said container body; and
        a connecting duct which connects, for fluid communication, the upper region of said first water head section to the lower region of said second water head section, whereby said first and second water head sections are series-connected to each other through said connecting duct.

11. The water-head suction adjustment valve of claim 10, further comprising a first water inlet located at the upper region of said first water head section, and a second water inlet provided at the upper region of said second water head section, wherein a water head of selectable height is providable by introducing a correspondingly selected amount of liquid, through said first and second water inlets, in said first and, respectively, second water head sections.

* * * * *